US011663756B2

(12) United States Patent
Menser et al.

(10) Patent No.: US 11,663,756 B2
(45) Date of Patent: May 30, 2023

(54) SCATTER CORRECTION FOR X-RAY IMAGING

(71) Applicant: KONINKLIJKE PHILIPS N.V., Eindhoven (NL)

(72) Inventors: Bernd Menser, Hauset (BE); Peter Prinsen, Eindhoven (NL); Dirk Schaefer, Hamburg (DE); Jens Wiegert, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 374 days.

(21) Appl. No.: 17/057,127

(22) PCT Filed: May 28, 2019

(86) PCT No.: PCT/EP2019/063749
§ 371 (c)(1),
(2) Date: Nov. 20, 2020

(87) PCT Pub. No.: WO2019/229032
PCT Pub. Date: Dec. 5, 2019

(65) Prior Publication Data
US 2021/0192807 A1    Jun. 24, 2021

(30) Foreign Application Priority Data

May 29, 2018    (EP) .................................... 18174785

(51) Int. Cl.
*G06T 11/00*    (2006.01)
*A61B 6/00*    (2006.01)

(52) U.S. Cl.
CPC ........... *G06T 11/005* (2013.01); *A61B 6/5282* (2013.01); *G06T 2207/10081* (2013.01); *G06T 2207/10116* (2013.01)

(58) Field of Classification Search
CPC ......... G06T 11/005; G06T 2207/10081; G06T 2207/10116; A61B 6/5282
See application file for complete search history.

(56) References Cited

U.S. PATENT DOCUMENTS 10,292,672 B2    5/2019    Kawamura
10,762,384 B2    9/2020    Ito
(Continued)

FOREIGN PATENT DOCUMENTS

| EP | 1476077 B1 | 9/2009 |
| JP | 2016198469 A | 12/2016 |
| WO | WO2007148263 A1 | 12/2007 |

OTHER PUBLICATIONS

PCT International Search Report, International application No. PCT/EP2019/063749, dated Jul. 31, 2019.
Wiegert J. at al., "Model Based Scatter Correction for Cone-Beam Computed Tomography", Medical Imaging 2005: Physics of Medical Imaging, edited by Michael J. Flynn, Proceedings of SPIE vol. 5745, Apr. 20, 2005.
(Continued)

*Primary Examiner* — Vu Le
*Assistant Examiner* — Winta Gebreslassie
(74) *Attorney, Agent, or Firm* — Larry Liberchuk

(57) ABSTRACT

An image processing system (IPS) and related method. The system (IPS) comprises an input interface (IN) for receiving an image (IM) of an object (OB) acquired by an imaging apparatus (IA). A kernel provider (KP) of the system (IPS) is configured to provide respective scatter kernels for at least two scatter types. A scatter correction module (SCM) of the system (IPS) is configured to perform a correction in the image based on the provided at least two kernels.

10 Claims, 6 Drawing Sheets

(56) References Cited

U.S. PATENT DOCUMENTS

| | | |
|---|---|---|
| 2008/0013673 A1 | 1/2008 | Ruhrnschopf |
| 2008/0075347 A1 | 3/2008 | Ruhrnschopf |
| 2008/0159469 A1 | 7/2008 | Ruhrnschopf |
| 2009/0202127 A1* | 8/2009 | Bertram ............... G06T 11/005 382/131 |
| 2010/0119139 A1 | 5/2010 | Bertran |
| 2010/0189376 A1 | 7/2010 | Bertram |
| 2012/0236983 A1 | 9/2012 | Star-Lack |
| 2013/0170722 A1* | 7/2013 | Star-Lack ............ G06T 11/005 382/131 |
| 2015/0170359 A1 | 6/2015 | Star-Lack |
| 2016/0296192 A1 | 10/2016 | Noda |
| 2018/0014806 A1 | 1/2018 | Lu |
| 2020/0205765 A1* | 7/2020 | Koehler ............... A61B 6/5282 |
| 2023/0007835 A1* | 1/2023 | Ratcliffe ................. G06T 7/12 |

OTHER PUBLICATIONS

Zhao W. et al., "A Model-Based Scatter Artifacts Correction for Cone Beam CT", Department of Biomedical Engineering, Huazhong University of Science and Technology, Hubei, China, and Stanford University, Department of Radiation Oncology, Feb. 29, 2016.

Star-Lack J. et al., "Efficient Scatter Correction Using Asymmetric Kernels", Proceedings of SPIE—The International Society for Optical Engineering, Feb. 2009.

Megert J. et al., "Improved CT Imaging Quality Using a New Fully Physical Imaging Chain", SPIE Medical 7622, Mar. 22, 2010.

Sun M. et al., "Improved Scatter Correction Using Adaptive Scatter Kernel Superposition", Physics in Medicine and Biology, Phys. Med. Biol. 55, Apr. 7, 2010.

Metropolis N. et al., "Equation of State Calculations by Fast Computing Machines", Journal of Chemical Physics, vol. 21, No. 6, Mar. 6, 1953.

* cited by examiner

A)

B)

SCATTER CORRECTION FOR X-RAY IMAGING

FIELD OF THE INVENTION

The invention relates to an image processing system, to an image processing method, to an imaging apparatus, to a computer program element and to a computer readable medium.

BACKGROUND OF THE INVENTION

X-ray imaging is one of the most important imaging modalities for diagnostic or interventional purposes in the medical field, although X-ray imaging is also used in other field, such as material testing, etc.

Having high contrast X-ray imagery available, in particular for the diagnostician, allows reducing diagnostic error rates. Scatter is a phenomenon that occurs during X-ray imaging and is known to reduce image quality, in particular X-ray contrast. A scatter corruption can hide possibly crucial image detail and thus may lead to misdiagnosis such as in mammography where delicate micro calcifications are sometimes examined.

Various mechanisms have been proposed in the past to combat the effect of scatter. One such approach is using anti-scatter grids (ASG) that are designed to block out at least some of the scattered radiation. Other approaches are based on image processing, some of which are kernel based. In these approaches, certain functions are used to approximate the effects of scatter. In these methods, the scattered radiation of a pencil beam through the scatter of certain basic shapes, for example homogeneous water balls of different sizes, is determined in advance. The scatter in a real X-ray image is then estimated by finding for each beam section a locally best matching ball, for example based on signal strength and signal gradient, and using the scatter generated by that ball as an estimate for the real scatter created by the primary beam in that location. Kernel-scatter modelling based on water balls is discussed in Applicant's WO 2007/148263 A1.

SUMMARY OF THE INVENTION

There may be a need in the art to further refine or improve X-ray scatter correction.

The object of the present invention is solved by the subject matter of the independent claims where further embodiments are incorporated in the dependent claims. It should be noted that the following described aspect of the invention equally applies to the image processing method, to the computer program element and to the computer readable medium.

According to a first aspect of the invention there is provided an image processing system (IPS), comprising:

an input interface for receiving an image of an object acquired by an imaging apparatus;

a kernel provider configured to provide respective scatter kernels for at least two scatter types; and a scatter correction module configured to perform a correction in the image based on the provided at least two kernels.

A kernel is a function, explicit or implicit that derives from a real or conceptual test object (also known as a "phantom"). The kernel can be said to be associated with the phantom. The kernel is a point spread function (PSF). The PSF is in general a 2D-scalar field that describes how the phantom spreads a pencil beam around a certain image location of a detector. The kernel describes scatter behavior of the phantom. If the object to be imaged (which is different from the phantom) at least locally corresponds to the phantom, the assumption is that similar point spread or scatter behavior may be expected. The kernel, being a 2D scalar field, may be considered as an image, which may be referred to herein as "scatter image" to distinguish some from the image of the actual object.

The at least two scatter types involve, respectively, a different number of scatter events. In preferred embodiments, the scatter types include a single scatter event and the other scatter type includes multiple scatter events.

It has been found that estimation of single scatter event depends almost exclusively on characteristics of the imaged object close to the primary beam, while estimation of multiple scatter also depends on characteristics further away. We therefore propose herein to split scatter kernels into a single scatter kernel and a multiple scatter kernel. This offers the advantage of being able to use different object characteristics for single scatter kernel selection and multiple scatter kernel selection. One may hence optimize better for type of scatter, rather than optimizing for combined scatter events. In other words, a more refined scatter modelling is proposed that distinguishes the different scatter types, in particular single and multiple scatter, thereby affording better scatter correction over approaches where no such distinction is made.

The providing by the kernel provider may include matching the associated phantoms for the two different sets of pre-computed kernels against image information in the input image (or information related thereto such as gradients, filtered or clipped signals or gradients, etc). The different sets include kernels obtained by simulating single scatter events and kernels obtained by simulating multiple scatter events, respectively. In each set, the respective kernels may be further stratified according to size/shape of the associated phantom or material type. Preferably a water based phantom is used for simplicity.

The kernel provider is configured to select or compute the at least two kernels differently to better account for the different characteristics of the two scatter types. At least one kernel of the at least two kernels can therefore be selected differently. Examples and embodiments of how the kernel provider is configured to select or compute the at least one kernel of the at least two kernels differently are described in more details below.

The selection or computation of the single scatter type kernels follows preferably a local approach whilst the selection of the multiple scatter type kernels follows either a local approach (but different from the local approach for single scatter) or a global approach.

Specifically, in embodiments, the kernel provider is configured to select or compute the at least one kernel for a single scatter event based on signal strength and/or signal gradient in a given patch (or subset) in the image. In addition or instead of signal strength or signal gradient, other image features in the input image may be used to guide the kernel selection by the kernel provider, such as filtered gradient, or signal values or functions of signal values in a larger pixel neighborhood.

In embodiments, the kernel provider is configured to provide the at least one kernel for multiple scatter events based on a clipped signal gradient in the given patch of the image.

In embodiments, the kernel provider is configured to provide the at least one kernel for multiple scatter events based on, first filtering the image and then considering the signal strength and/or gradient in the given patch of the filtered image. The filtering includes low-pass filtering. A purpose of the filtering or gradient clipping is to ensure that the fitting operation is less sensitive to high spatial frequency structures, which are more relevant for single scatter than for multiple scatter.

Turning now to the global approach, in embodiments the kernel provider is configured to provide the at least one kernel for multiple scatter events based on signal strength and/or signal gradient of the whole image.

In embodiments, the kernel provider is configured to provide the at least one of the kernels based on a physical characteristic of the object. This is of particular benefit for the multiple scatter event type kernel selection. Specifically, to better account for the more global reach of multiple scatter, the kernel provider is configured to provide the at least one kernel for multiple scatter events based on a shape or size of at least a part of the object.

In embodiments, the kernel provider is configured to provide at least one of the kernels based on a library of pre-computed kernel types.

In embodiments, a further refinement is envisaged wherein the system includes a tissue determiner configured to determine a tissue type based on the image, wherein the kernel provider takes the tissue type into account when providing at least one of the at least two kernels. This allows obtaining still more accurate scatter correction, in particular, for objects with heterogeneous density distribution which may be caused by the presence of bones in the imaged anatomy. More specifically, while the mass attenuation coefficients for photoelectric effect and Compton scatter of soft tissue are very similar to the coefficients of water, X-ray absorption and scattering properties of bone are very different. In other words, for the same primary absorption, scatter from a water object is larger than the scatter from a bone object. The tissue determiner allows forming scatter kernels that are adapted to the local material composition to so account for the different scattering properties of, in particular, bone and soft tissue.

According to a second aspect, there is provided a method of image processing, comprising:

receiving an image of an object acquired by an imaging apparatus;

providing respective scatter kernels for at least two scatter types; and performing a correction in the image based on the provided at least two kernels.

According to a third aspect, there is provided a computer program element, which, when being executed by at least one processing unit, is adapted to cause the processing unit to perform the method.

According to a fourth aspect, there is provided a computer readable medium having stored thereon the program element.

The input imagery may be drawn from projection domain but application of the proposed system and method to reconstructed imagery is not excluded herein. Scatter correction in image domain may be done performing first reconstruction from projection imagery, with a less accurate scatter correction. The scatter is then estimated as described above, but this time based on the reconstructed image. The corrected reconstruction may be used for a better choice of scatter kernels which are then used to produce more accurate scatter-free projection images that are then used for a second reconstruction. The proposed method has been shown to be of particular benefit in chest/lung imaging where spongy tissue with pockets of air inclusions such as lung tissue is in close proximity to high density tissue, such as bone.

Although the present disclosure is mainly concerned with medical X-ray imaging, non-medical applications are not excluded herein, such as baggage screening, or non-destructive material testing.

References in this disclosure to "1D", "2D" or "3D" are shorthand for spatial one-, two- or three-dimensionality, respectively.

BRIEF DESCRIPTION OF THE DRAWINGS

Exemplary embodiments of the invention will now be described with reference to the following drawings, which are not to scale, wherein.

DETAILED DESCRIPTION OF EMBODIMENTS

Figures 1, 1A:
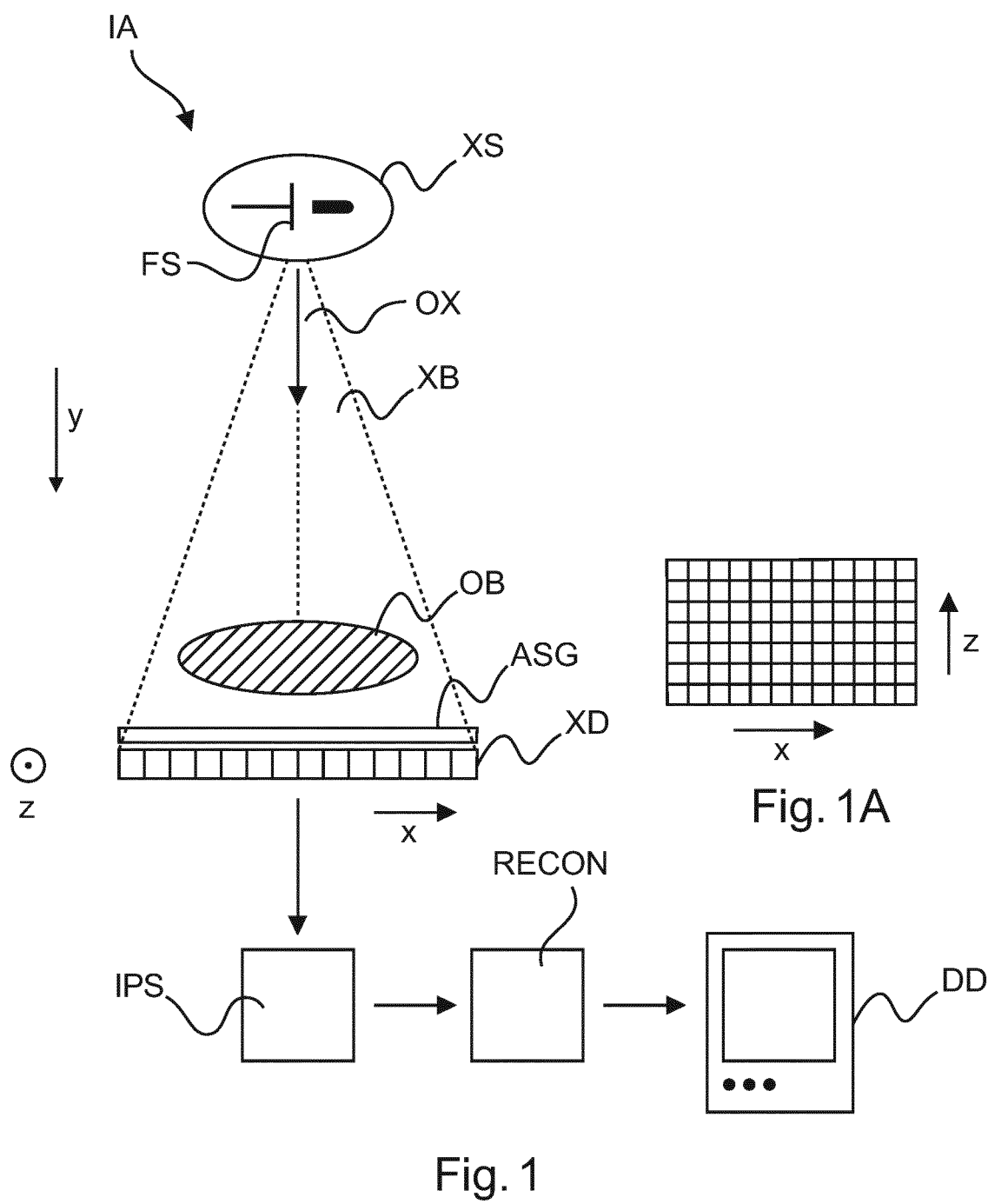
FIG. 1 shows a schematic block diagram of an imaging arrangement.

With reference to FIG. 1, this is a schematic diagram of an X-ray imaging arrangement comprising an X-ray imaging apparatus IA and image processing system IPS.

The imaging processing system is configured to process image data IM provided by imaging apparatus IA as will be explained in more detail further below.

Turning first to the imaging apparatus IA, this is shown in schematic side elevation view in FIG. 1. Embodiments of the imaging apparatus IA include a C-arm imaging apparatus, a CBCT (Cone Beam CT) scanner, a CT scanner, a mammography apparatus or a radiography apparatus, or other, configured to acquire an X-ray image IM of an object OB.

The object OB is shown in cross-section with an imaging axis z. In FIG. 1, the imaging axis z extends into the drawing plane. Although main applications for the X-ray imager envisaged herein are in the medical field, non-medical contexts such as non-destructive material testing or baggage screening, etc. are not excluded herein. Accordingly, the term "object OB" is used herein in the general sense to include animate "objects" such as a human or animal patient, or anatomic parts thereof but also includes inanimate objects.

In more detail, the X-ray imaging apparatus IA includes an X-ray source XS and an X-ray sensitive detector XD. In use, the object OB is positioned along axis z in an examination region within the X-ray source XS and the X-ray detector XD. The X-ray source XS is energized to produce an X-ray beam XB which emanates from a focal spot FS and traverses the examination region and hence at least a region of interest of the object OB. In FIG. 1, OX is the optical axis, and the main propagation direction of the X-ray beam XB, with axis y parallel to OX Specifically, the optical axis OX runs from the focal spot FS to detector XD and intersects the detector D at a point. The image surface has coordinates x,z, with x being orthogonal to imaging axis z, and both, x,z, being orthogonal to the optical axis OX or axis y.

The X-radiation interacts with matter (e.g., tissue, bones, etc.) of the object OB. After interaction, the X-radiation emerges at the far side of object OB to then impinge on the X-ray detector XD. The impinging X-radiation is detected by the detector XD and converted into electrical signals. The electrical signals are converted by suitable conversion circuitry (not shown) into image values which may then be processed into X-ray images by an image processor IPS. The image values may be arranged in rows and/or columns which form the X-ray image. Suitable imaging software may be used to visualize the imagery on one or more display devices DD. The images may also be stored or otherwise processed. The X-ray images are capable of revealing details of the internals of the imaged object OB. This can help in diagnosis and therapy or other examination of the imaged object OB.

The X-ray image provided by the X-ray imaging apparatus is either a projection image or reconstructed imagery. Traditional radiography is projection image-based. Reconstructed imagery emerges for instance in the context of CT or C-arm imaging. In which case the signal processing chain includes a re-constructor RECON that runs a reconstruction algorithm such as filtered back-projection or other. The re-constructor RECON processes the projection imagery which is located in the plane of the detector and converts the projection imagery into one or more slice images that are located in the image domain or the examination region in the plane perpendicular to that of the detector plane. The re-constructor hence maps projection imagery from the projection domain into slice imagery in the image domain. It will be understood that in general multiple projection images are acquired from different directions of the objects. In CT this is achieved by a rotational arrangement where the X-ray source and/or the detector rotates around the object OB to acquire this set of multiple projection imagery along different directions. It is this set of projection imagery that is then fed into the re-constructor RECON to obtain one or more slice images which can be thought of as making up together an image volume that is an image approximation of the examination region that includes the object OB.

The imager IA may also include a collimator (not shown) situated at the X-ray source to shape the X-ray beam to better conform with a region of interest to be imaged. The detector XD may be a flat panel detector, but curved embodiments are also envisaged herein. The detector XD may be of the direct conversion type or of the indirect conversion type.

In inset FIG. 1A there is shown, in plan view, a schematic grid layout that represents an image surface of the X-ray detector XD with axes x,z and the four outer edges of the image surface. Axis z is the imaging axis as introduced above. The small squares in the grid layout of FIG. 1A represent detector cells or pixels that are arranged in multiple "rows" (by convention, along direction x) and "columns" (by convention, along direction z). Alternatively, single line/row detectors are also envisaged herein in the alternative.

As mentioned, the image surface may be planar as shown in FIG. 1A or may instead be curved to form a partial lateral surface of an imaginary cylinder with longitudinal axis (referred to hereinafter as "axis of curvature") through focal spot FS of the X-ray source XS and parallel to axis z. In these embodiments, the image surface of the detector XD is focused as a whole to the focal spot of the X-ray source XS.

When viewed from the focal spot FS, on top of the X-ray detector there may be arranged an anti-scatter grid ASG to reduce exposure to scatter radiation. The ASG comprises strips formed from radiation-opaque material. The strips are arranged in one set in parallel, with the strips' respective longitudinal edges directed towards the X-ray source XS. The strips may have their faces arranged in parallel. Alternatively (not shown in FIG. 1 or 2), the faces are not in general parallel but angled so that the strips are focused towards the focal spot. In this case, imaginary planes, that are respective extensions of the strips, intersect in an imaginary line. The imaginary line runs through the focal spot and parallel to the z axis.

In the side elevation view of FIG. 1, the strips run along axis z, into the plane of the drawing. This arrangement is commonly referred to as 1D. Alternatively, there is a 2D layout, with two sets of strips. Strips are parallel in one set (say along x) and run across the second set of strips which are parallel to axis z. Alternatively, a 1D layout may be folded into a 2D layout.

The proposed imaging arrangement, as envisaged herein, includes preferably two mechanisms to reduce the adverse effects of scattered radiation on imaging results. One mechanism is the above mentioned anti scatter grid ASG which forms a hardware defense against scatter. Instead of an ASG, preferably in addition thereto, there is also a second scatter reduction mechanism in the form of the above mentioned processing system IPS. If unaccounted for, scattered radiation (referred to herein simply as "scatter") is known to lead to lower image quality, in particular lower contrast.

The image processing system IPS is configured to reduce scatter effects on the imagery by computing correction values which are then applied to the imagery IM. In other words, the image processing system IPS acts computationally to reduce the effects of scatter.

Figure 2:
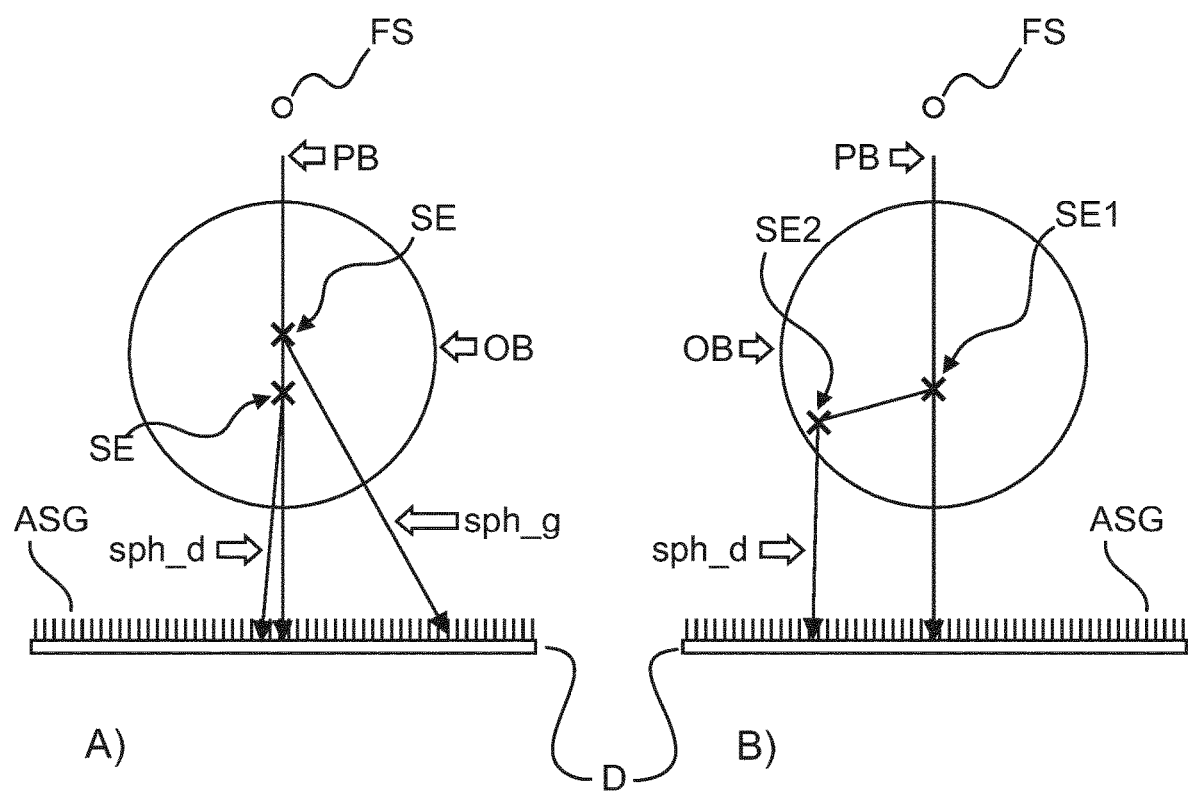
FIG. 2 shows an illustration of single and multiple scatter events.

Before explaining operation of the proposed image scatter reducing system IPS in more detail, reference is now made to FIG. 2 where the scatter phenomenon is looked at in more detail.

Scatter is one mode of interaction between matter and x-radiation, the other being absorption. There are also other modes not considered herein such as phase changes. The scatter phenomenon itself may be classified as small angle (or Rayleigh)-scattering and Compton scattering. The following discussion may focus on Compton scattering.

The X-radiation beam XB emanating from the focal spot FS can be thought of as a diverging bundle of individual pencil beams that propagate along a set of respective imaginary geometrical rays that can be cast from the focal spot FS to the different detector pixel positions on the detector D. X-ray photons travel along respective ones of the geometrical rays to form those pencil beams. The photons, prior to impacting with matter, have an initial energy when they emerge from the focal spot FS of the X-ray source XS. Some photons travelling along a given geometrical ray are absorbed thus reducing the intensity of the X-radiation seen at the respective detector pixel located at the end of the respective geometrical ray. However, not all of the reduced intensity can be attributed to absorption events. Other photons in the given pencil beam may get scattered, so diverge off their intended path along the geometrical ray as shown in FIG. 2A. One such geometrical ray, or intended path of a pencil beam PB, is shown as a bold arrow that intersects the detector plane at a given pixel. Because of a scattering event SE the photon diverges off the intended path and is instead incident at another detector pixel in relatively close neighborhood of the intended pixel. Therefore, a certain amount of intensity that should have been seen at the intended pixel is instead registered at another pixel location as a scattered photon sph_d. But, if the scatter event is such that the photon diverges off its intended path by more than a certain angle, as shown by scatter photon sph_g it is then filtered out by the strips of the ASG. The situation in FIG. 2A reflects the proposition that there are only single scatter events for any given photon. Under this assumption, singly scattered photons are either registered locally in a neighborhood around where the geometrical ray for given photon intersects the detector D, or are not registered at all due to the ASG's filter action.

However, as shown in FIG. 2B, a photon may well encounter multiple scatter events such as SE1 and SE2. In the case of multiple scatter events a photon sph_d will then not necessarily be filtered out by the anti-scatter grid and is detected instead at a detector pixel position relatively far away from the intended pixel location where the geometrical ray of its initial path intersects the detector D.

In other words, scatter can be distinguished into two types, single scatter events and multiple scatter events. Each of them impacts differently on the detector and hence contributes differently to the overall radiation measured by the detector: multiple scatter events tend to contribute globally to the measurements, whilst single scatter events contribute more locally. In the following, for brevity, single scatter events may also be referred to as scatter of the "first type/category" and multiple scatter events as scatter of the "second type/category".

Figure 3:
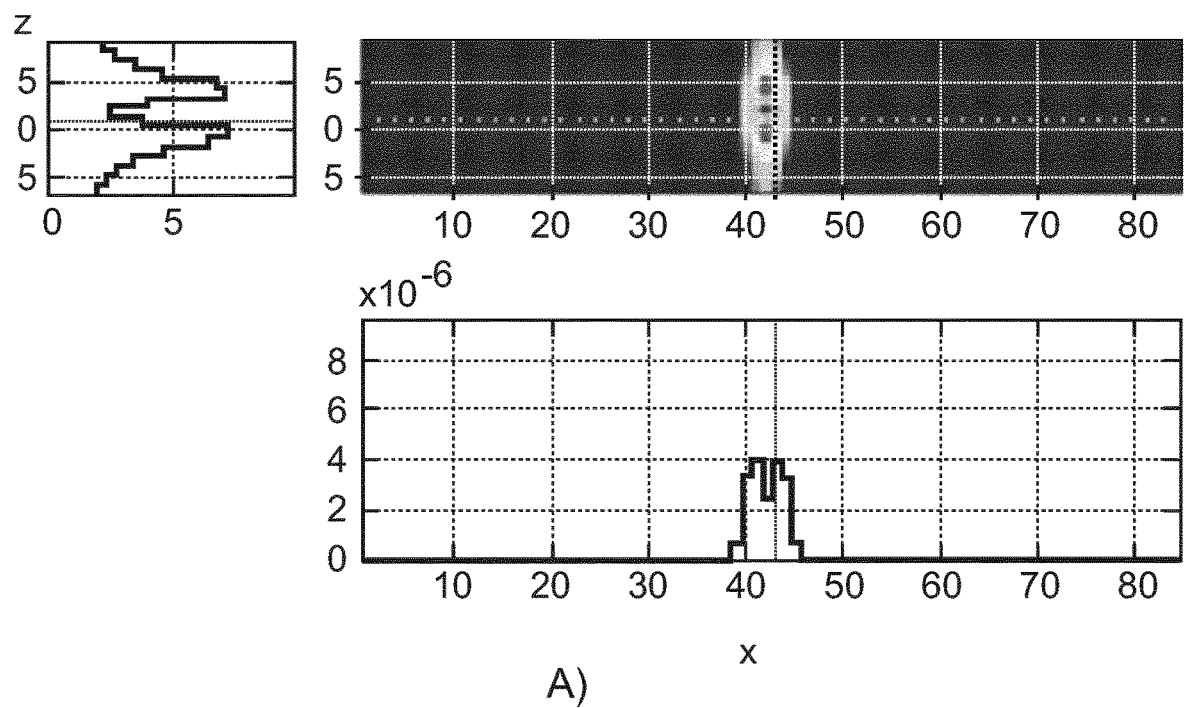
FIG. 3 shows point spread imagery of single A) and multiple B) scatter events.
Figure 3:
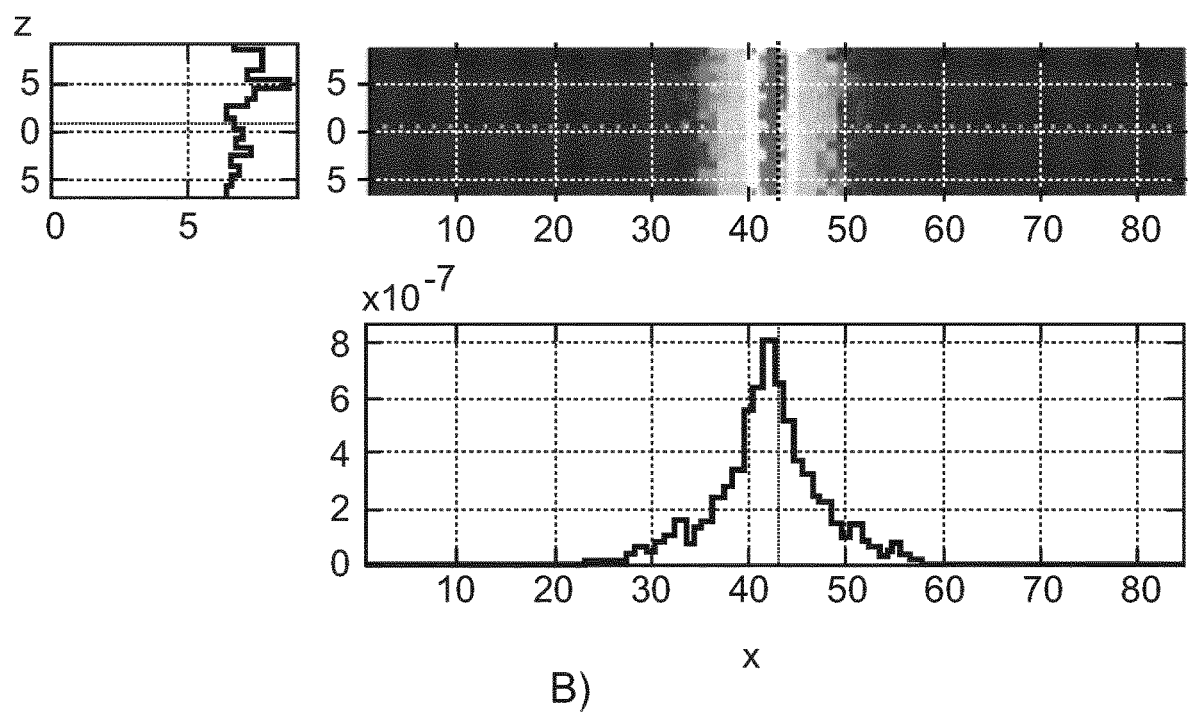

Examples of the point spread functions PSF for the two types of scatter are illustrated in FIG. 3A,B, with Fig. A showing point spread function of a single scatter event whilst FIG. 3B to the right shows a multiple scatter event point spread. The projection imagery in the detector plane shown in FIG. 3A, B is in plan view, as viewed above from the focal spot FS. The adjoined respective diagrams show intensity profiles in x and z directions, respectively. Single scatter event leads to more concentrated point spread functions, whilst multiple scatter event leads to more spread-out, point spread functions with a broader ridge.

The image processing system IPS proposed herein is configured to account differently for the two types of scatter, multiple and single. The image processing system IPS is configured to computationally act differently on the to be corrected imagery IM to so account for the two types of scatter. More specifically it is proposed herein to refine a scatter model that is capable of distinguishing between multiple and single scatter events.

Figure 4:
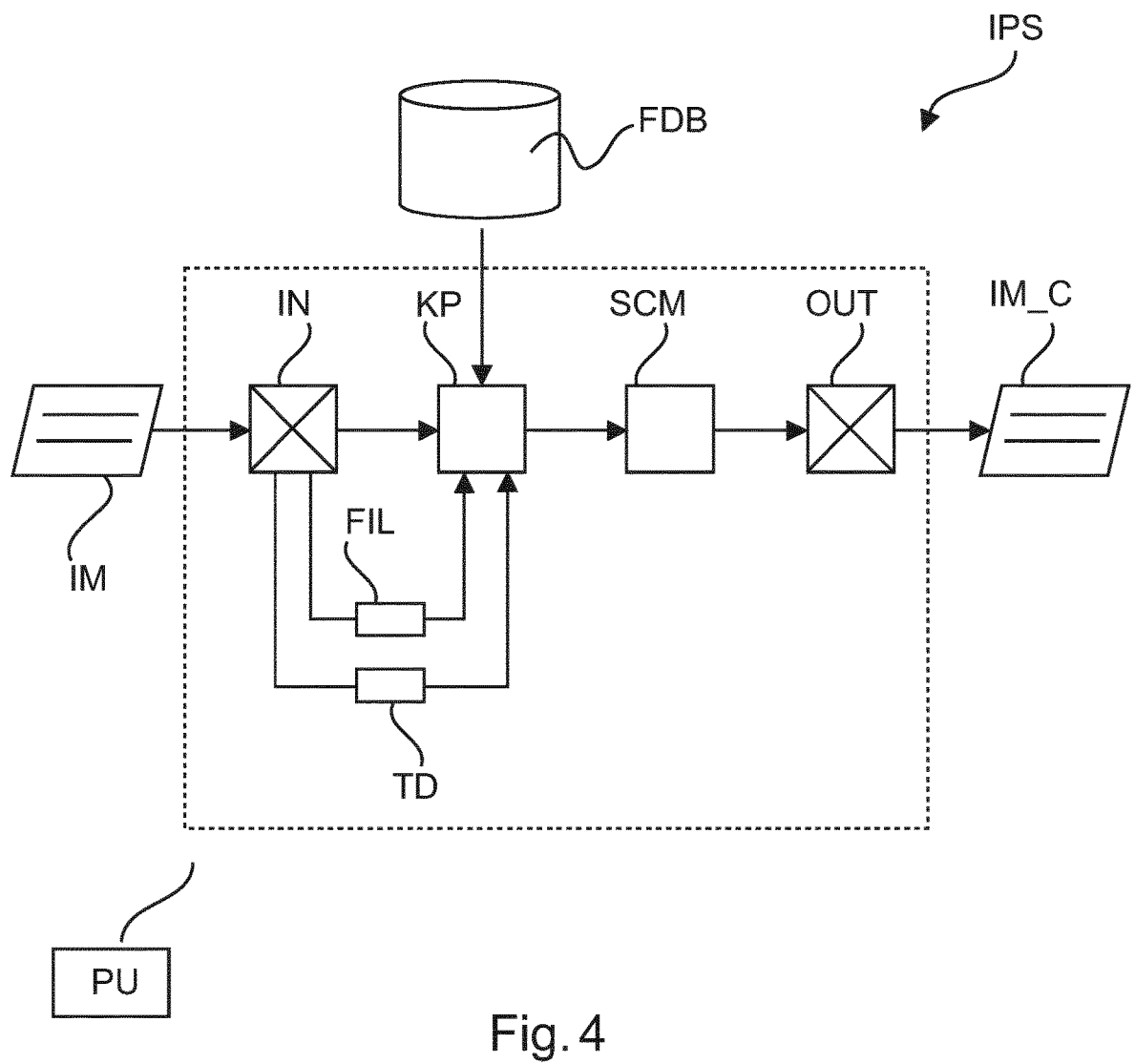
FIG. 4 shows a schematic block diagram of an image processing system envisaged herein in one embodiment.

A schematic block diagram of the proposed processing system IPS is shown in FIG. 4. The image processing system can be arranged to process projection imagery as received from the detector. Alternatively, the image processing system may also act on reconstructed imagery. The input image IM (that is, the projection image or re-constructed image) is received at the input port IN of the image processing system IPS. In embodiments the proposed image processing system is kernel based, in other words it uses approximations of scatter point spread functions PSF to compute the correction values. In embodiments the kernels are pre-computed and held in a data base FDB.

As envisaged herein, a kernel provider KP provides, respectively, dedicated kernels for single scatter and multiple scatter that each fit the signals as recorded in the input imagery IM. The kernels for the two types of scatter are used to estimate, respectively, the single scatter contributions and multiple scatter contributions as recorded in the input imagery. The so estimated amounts of multiple and single scatter are then applied to the input imagery IM by corrector module SCM. Preferably the estimated amounts of multiple and single scatter are subtracted point-wise from the input image IM. The corrected image IM_C is then output at output port OUT. IM_C can then be visualized, stored or otherwise (further) processed.

The kernels held in database FDB are of two types, namely those for single scatter events and those for the multiple scatter events. In addition, for each kernel type or category, single or multiple scatter, there is further stratification according to size and shape of certain sample bodies from which the respective kernels have been pre-computed. Consistent with the earlier introduced shorthand of first and second type scatter, we may accordingly refer herein to kernel of "first" or "second" type, depending on whether the kernel is configured to capture characteristics of single or multiple scatter, respectively.

Figure 5:
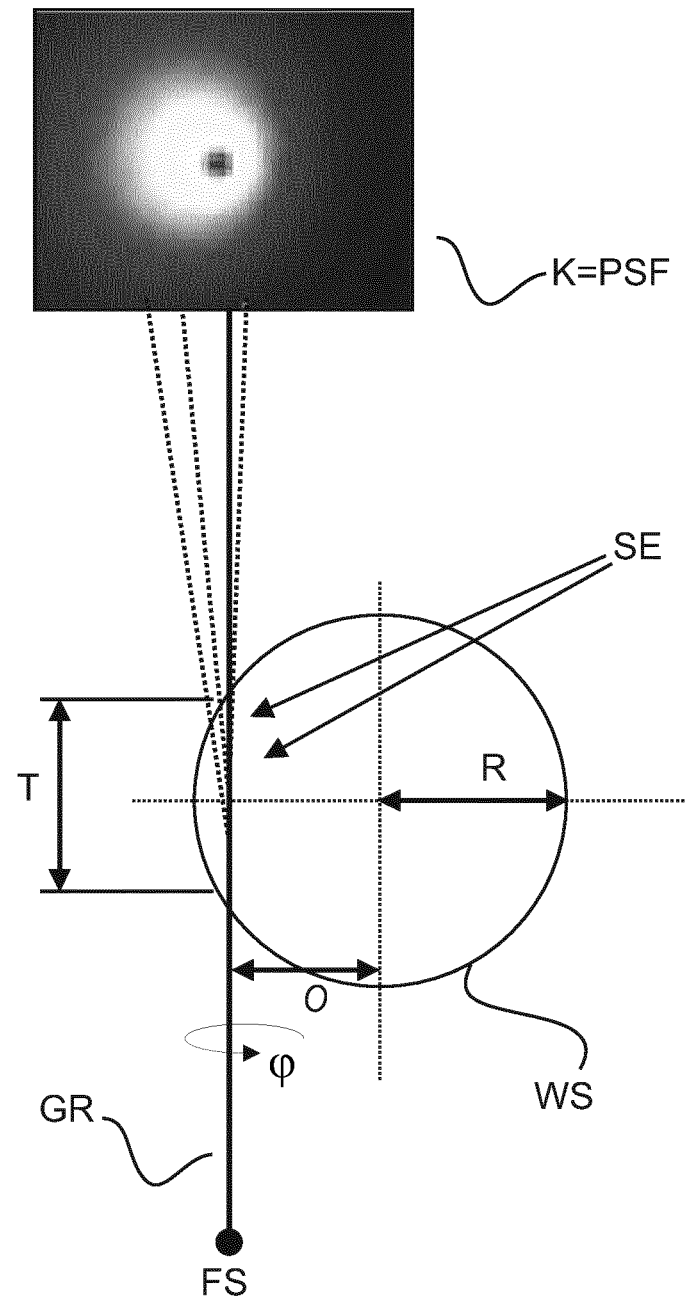
FIG. 5 shows a kernel model as envisaged herein in one embodiment.

In one embodiment the sample bodies or phantoms can be thought of as models of balls of water (or of other material) which are shown in side elevation and schematic fashion in FIG. 5. Apart from recording intensities, the image values in the input image also record gradients which are approximations of local differences between the image values. Gradients represent tissue transitions or tissue-air transitions in the object OB or changes in thickness of the imaged patient, especially towards an edge or a border portion.

In order to model different intensities and gradients the sample phantoms WS are parameterized by three parameters as shown in FIG. 5. One parameter, R, parameterizes the size of the phantom body WS. In the case of balls, such as water balls, R is the radius thereof. Another parameter, φ, parameterizes the relative arrangement of the phantom body WS to the strips of the anti-scatter grid ASG. This can be described by rotation angle φ around the geometrical ray GR that passes through the body WS. The third parameter is the path length T along ray GR through the phantom body WS. The path length is determined by offset O away from the given ray GR for a given location. The path length T allows modelling different gradients. The set of parameters may be distinguished into two components: one or more for the size of the phantom (such as parameter R in the ball shaped phantom embodiment) and one or more components (such as T (or O) and φ) that relate to the relative position of the phantom to the respective image location. The earlier component may be called the "size component". Again, this concept may be generalized to phantoms of any shape, the balls being one embodiment.

For each set of parameters (T, φ, R) [or (O, φ, R)], the kernel, also known as point spread function PSF, can be obtained either experimentally or preferably by theoretical simulation, as the material properties of the phantom body (density, Z-number), such as water, are known. The kernel or point spread function PSF can be considered a "scatter signature" of the parameterized phantom body WS. As explained in more detail below, the kernel emerges as the scatter caused by a conceptual pencil beam to which the phantom is exposed. The kernel then describes the scatter caused by the phantom WS versus pencil beam interaction and how this scatter manifests itself in terms of image structure. The point spread function PSF, being a 2D scalar field, can itself be represented as a "scatter image". Kernels for a range of different phantom bodies WS with different parameters are preferably pre-computed. The parameters (T, φ, R) are incremented in suitable steps to obtain a whole library of kernels.

One way of obtaining the kernels based on simulation is now explained in more detail. Unlike earlier approaches, such as in WO 2007/148263A1, the kernel library proposed herein is refined by computing different kernels for single scatter events and multiple scatter events, respectively.

Computing these different kernel types can be done by running a Monte Carlo (MC) simulation based on each of the parameterized kernels WS. In the MC simulation individual photons as pencil beams are simulated that start at the source FS. These are then tracked throughout the simulation until they are i) absorbed by the phantom WS, or ii) hit the detector (or anti scatter grid) or iii) exit the simulation volume. Interactions of photons with materials are probabilistic, and the probabilities and probability distributions are known from theory, these being a function of the photon energy, the density of the phantom material and the material type in terms of Z-numbers. Water and its properties are preferably used. One then randomly selects a path for the photon from its current position to the next interaction, whilst this random selection is done according to the correct probability distribution. This is done for each photon until any of the above defined events i)-iii) occurs. This way, one knows for each photon that hits the detector exactly how many times it has interacted before. This tracking and simulation is done for a large number of simulated photons.

The simulation may be efficiently implemented using the Metropolis-Hastings algorithm (or variants thereof), first reported by N Metropolis et al in "*Equation of State Calculations by Fast Computing Machines*", Journal of Chemical Physics. 21 (6), pp 1087-1092.

The number of simulated photons can be in order of $10^5$ or even $10^6$ or more. All simulated photons that hit the detector may then be divided into two groups: a group that interacted once before hitting the detector, and a group that interacted multiple times. These two groups are then used to create the two kernel categories. Specifically, the signals for photons as detected in the single interaction group then together form the PSF for single scatter events for the specific parameterization of the phantom WS. And photons as detected in the multiple interactions group then together form the PSF for multiple scatter events for the specific parameterization of the phantom WS. The above simulation may then be repeated for different kernel parameterizations, by changing the parameters increments (eg, different R's, different $\varphi$, different T in the water ball model WS) to thereby build up the two-tier kernel library.

It will be understood from the above, that each phantom WS (identifiable via its parameterization i) is associable with two respective kernels or "scatter images", one for multiple scatter and one for single scatter. In addition, each phantom is also associable with another data component which may be called a respective "ideal image". It follows then that each kernel is associable with the respective ideal image of the given phantom WS. This ideal image is derivable when exposing (theoretically or experimentally) the respective phantom WS to a full beam (and not merely a pencil beam) and when scatter effects are neglected. Such ideal images can be obtained by an MC simulation. Alternatively, one may directly relate image features (signal level and/or signal gradient) of the ideal image to the spatial parameters (eg, (T, $\varphi$, R) or (O, $\varphi$, R) for the exemplary water ball embodiment) of the phantom WS as has been shown in Applicant's US 2010/0189376, eqs (2) and (3) therein. In this later embodiment, no simulation is required. In addition to pre-computing and storing the kernels of the two categories, it is preferable to likewise pre-compute and store the respective ideal images for each phantom.

In this manner we obtain for each parameterization a separate kernel PSF, one for single scattering events and one for multiple scatter events. The kernel library FDB may hence be organized in two-tier fashion, including kernels of first and second type, each type stratified by different parameters (T, $\varphi$, R).

It should be noted that basing the above on water balls is not a necessity herein: other shapes and/or other materials may also be considered. Indeed, as will be explained in more detail below instead of using balls or spheres in embodiments the shape of the phantoms to generate the kernels PSF is chosen according to the body type or region of the body to be imaged.

As mentioned earlier, in one embodiment the kernels of the two types, single scatter and multiple scatter, are pre-computed and stored in the database. However, alternatively the kernels may be computed on demand, on the-fly. This may be achieved for instance by using suitably tuned dedicated processors, such as ASICs etc. Preferably, however, the kernels are pre-computed to decrease turnaround time so that the scatter corrected image IM_C can be produced more quickly during deployment.

In embodiments, the kernel provider KP is configured to select and optimize kernels separately for single and multiple scatter events respectively. This allows optimizing individually and separately for scatter event type, rather than choosing one kernel to account for both scatter types. As earlier observed, single scatter events have a more local effect around the considered image location, whilst multiple scatter events have a more global reach. This distinction between global and local reach is preferably reflected in the proposed system IPS by the separate selections of kernels for the two types, single and multiple scatter. Accordingly, the kernel provider operates in two-stages.

The kernel selection in either stage is generally done via the phantoms, more particularly via the associated ideal images of the phantoms. The ideal images are matched against the patches in the input image. Once a best match is found, the kernel associated with the best matching ideal image is then selected for the given patch, and procedure is repeated for some or all patches throughout the input image. It is the selected kernel that then forms the single or multiple scatter event estimation of the pencil beam associated with the given patch. The scatter image is in general larger the considered patch.

Turning now first to the first stage where the kernel provider KP operates to select single scatter event kernels, for some or each image location in the input image a suitable image patch is defined, for instance a square of 10×10 pixels. Other patch sizes or shapes are also envisaged. Patch size and shape is in general a function of the kernel sizes and shapes held in the database FDB.

The image information in the recorded image IM in the respective patch is then used to find a best matching kernel from the single event category as stored in database FDB. An optimization algorithm may be run to find the kernel that best matches the concerned image patch. In one embodiment this can be simply done by iterating through all kernels in the first category and comparing the respective difference image formed by taking the respective pixel-wise difference between each of the ideal images of the phantoms WS used to compute the kernels and the image patch. As mentioned above, the ideal image is the image that the respective phantom WS would cause on the detector (or detector patch) if there was no scattered radiation on the detector. The kernel that yields the smallest such difference image is then selected from the finite set of pre-computed first category kernels in the library FDB, where "smallness" is measured by a suitable measure d. Suitable measures d include squared differences (summed over the patch or the whole areas), possibly weighted, or maximum difference value in the patch or others. The measure d may be defined purely on intensity as recorded in the image. Alternatively, or in addition, the patch may be used to estimate a local gradient in the respective pixel j that is hit by the pencil beam, for example by filtering, and matching this to the pixel intensity and/or gradient at that location j of the kernel.

However, for large kernel libraries the above mentioned approach of searching in the finite set of pre-computed kernels or phantoms may be too slow and an optimization scheme like conjugate gradients, gradient descent, Nelder-Mead or others may be used to minimize a cost function. The cost function F may be formulated in terms of the difference image and metric d as mentioned above which may be formalized as:

$$F^j(i) = d(P(IM)_j, K\_IM_i^1) \quad (1)$$

with optimization for the kernel $$K^{1\_j} = PSF_i^1.$$

where $$i^* = \operatorname{argmin}_i F^1 \quad (2)$$

wherein:

j is the considered image location;

i is an index/parametrization of kernels of the first type $PSF^1$, $P(IM)_j$ is the patch in input image around j; $K\_IM_i^1$ is the ideal image of the phantom on the detector (or patch thereof), $K^{1\_j}$ is the single scatter category kernel associated with the phantom that has an ideal image that best matches the real image patch (according to metric d); and $d(.,.)$ is a difference measure that quantifies the difference by mapping to a scalar.

In the water ball embodiments, i=(T, φ, R). In case the optimization (2) returns a parameter set i*=(T*, φ*, R*) for which no kernel is available, and this is likely to be the case in most instances, linear interpolation can be performed over i to interpolate the desired optimal kernel i* from the pre-stored ones. In this case it may be advantageous to store the pre-computed kernels in a linear look-up table LUT. Alternatively, the closest available kernel may be selected, possibly appropriately rescaled to match for example the total absorption of the pencil beam. In all the above and below embodiments, the locations j may refer to a physical pixel or non-physical pixel (such as after down-sampling).

In case shape primitives other than the above described ball model are used, such as ellipsoids or other, there may be more than three free parameters to fit. In this case, more image features from the image may be used. In embodiments, the equivalent water thickness of the 4 direct neighbors of a given pixel location j may be used to be able to fit for 5 parameters. Even more pixels from the neighborhood may be used to fit the "shape primitive" of the kernel to a local image patch. In general, the scatter kernel for a certain image location may be selected based on a group of pixels in the neighborhood using pixel values or a function (e.g. gradient) of their pixel values.

The above described fitting procedure for single scatter type kernels may then be performed for each and every location j in input image IM. However, in alternative embodiments, this may be simplified by coarsening the input image IM into sub-regions and performing the above described optimization scheme only per sub-region rather than per pixel j.

As further variant of the above described fitting procedures may also be envisaged, where based, on a sub-set of the parameters i, such as the size component(s), a best match is found, and this best match is then localized by optimizing the remaining parameters as per eqs (1), (2) for each location j.

Once all kernels for the single scatter event category have been computed, these can be used to perform pixel-wise correction of the input image IM to so correct for single scatter corruption. This may be done, for example, as follows:

$$IM\_C_p = IM - \Sigma_j K^{1\_j} \quad (3)$$

where j runs over all optimized first type kernels selected for respective image location, or sub-regions, etc. The selected kernels are summed and subtracted from the image IM. The image $IM\_C_p$ obtained at this stage may be called a partially corrected image as only the single scatter corruption has been accounted for so far.

The procedures in (3), (4) may be repeated iteratively for a predefined number of several steps or until convergence is reached.

Multiple scatter is taken care of at the next operational stage of the kernel provider KP. Separate from the first stage, in the second stage, the kernel provider KP now selects in general different kernels to match multiple scatter signatures in the image. The processing in the second stage is adjusted to the global characteristic of multiple scatter. Specifically, image gradients that are caused by multiple scatter events are expected to figure less prominently in the image IM and relate to more global structures with reduced spatial high frequency details. Based on this insight, in embodiments, the initial image IM is first subjected to a pre-processing by flattening the dynamics in the imagery. One way to do this and envisaged in embodiments, is to compute the gradients in the image and then clipping the gradient values at a pre-defined threshold. In this flattened image any contributions greater than the threshold are then removed.

Another way to obtain a flattened image is to run (local or a global) low pass filter(s) FIL on the initial image or partially corrected image. This filtering by FIL may be done in addition or instead to any other filtering (such as noise filtering) that may have already been done for other purposes further up-stream in the image processing chain. In particular, the filter module FIL for flattening has been set more aggressively, covering a larger part of the image than in any possible filtering that may have been applied to the image IM before performing the above described first stage. For example, preferably, the input image is filtered to get rid of noise. This noise-filtering is done locally with convolution kernel of a size that is smaller than the filter kernel sizes used for the above mentioned low-pass filter FIL.

Based on this flattened image, the kernels are now selected from the second category kernels in the library FDB, as described previously by defining image patches and finding the best match in terms of a measure d based on the above described optimization procedure in relation to (1), (2), but this time with second category point spread function $PSF_i^2$ instead of $PSF_i^1$ of the first type. If matching is gradient based, the low-pass filtering is performed first, and the gradients are computed after that. In either embodiment, the corrector module SCM then forms the corrected image IM_C by using all the selected second type kernels $K^{2\_j}$ to correct image $IM\_C_p$ for example as follows:

$$IM\_C = IM\_C_p - \Sigma_j K^{2\_j} \quad (4)$$

In alternative embodiments for selecting the kernels of the second type, the kernel matching is not performed for individual image patches but is performed on the whole image IM globally, based on image values or gradients. In this case a (single) best matching phantom, which may be referred to herein as a "global phantom", may be selected for the whole image, such that its parameters correspond best to the part of the patient that is to be imaged. In one embodiment (but not all embodiments), the fitting of the global phantom may be done by adjusting only a subset of the parameters. In one exemplary embodiment for this, only the size component may be adjusted to find the global phantom. More specifically, in the embodiments based on the water ball phantoms (or other ball shaped phantoms), only the radius R and/or offset O center location of the water ball model may be chosen so as to be approximately commensurate with the body part to be imaged, such as in head imaging.

Once the best matching global phantom has been chosen, kernels are selected for each pixel based on this best matching phantom and these are used to correct the image $IM\_C_p$, for example as in eq (4). More specifically, the size parameter of the global phantom is retained for each pixel location, whilst the remaining parameters, such as $\phi$ and/or T for the ball embodiment, are adjusted to achieve a local per pixel fit. For instance, for the ball embodiment in FIG. 5 above, the remaining parameters $(T,\phi)$ for each pixel follow from the radius R and, optionally, from the relative position O of the pixel with respect to the center of the ball.

Phantoms in shapes other than balls may be used instead. More particularly, ellipsoidal or cylindrical phantoms are particularly envisaged herein as these are better suited to fit chest, abdomen, or leg/arm imaging, respectively. In this embodiment the kernels held in the data base FDB are stratified not only in the two categories, but in the second category for multiple scatter events, there is a further stratification in terms of different parameterizations for different shape types such as any one or more of ellipsoidal, cylindrical, spherical, or other. In this embodiment the image processing system IPS may include a user interface configured to allow the user to specify the kernel shape to be used for a given image task. Alternatively, the selection of the kernel shape and size is automatically based on the image protocol specified by the user. Alternatively, spatial measurements such as diameter, major/minor axes, girth, length etc. of the region of interest is provided by the user through the user interface, preferably with a shape specification and the kernel provider then retrieves the best kernel size. Again, any of the above may be adapted if other phantom shapes or phantom materials are chosen in other embodiments.

The above described operation of IPS admits to a number of different variations, all envisaged herein. For instance, it may be understood that the second type kernel(s) $K^2$ may be selected first in the first stage, and it is the kernels of the first type that are selected later in the second stage. In addition, or instead, no partial image $IM\_C_p$ may necessarily be formed because the kernel selection in the two stages are both completed first, the selected kernels of the first and second type are then used at once to correct the input image IM_C.

However, for performance reason, the interleaved approach of first forming the partially corrected image $IM\_C_p$ by applying the first or second type kernels first, and then applying the kernels of the other type later may be preferred.

In embodiments where a partially corrected image $IM\_C_p$ is formed, it may be envisaged, as an alternative to the above, to base the selection of the kernels for the other type on the said partially corrected image $IM\_C_p$ instead of on the initial input image IM as described above. This may be preferably to achieve better correction results. More specifically, once the partially corrected image $IM\_C_p$ is gotten based on kernel selections of the first (or second) category, the matching of kernels from the second (or first) category is done based on the partially corrected image $IM\_C_p$. Preferably the procedure may be done iteratively, as will be explained in more detail below.

In embodiments a further refinement is envisaged where the kernel selection by the kernel provider KP is further refined by taking into account the tissue type present in the region of interest to be imaged. More particularly, in one embodiment bone tissue is taken into account by computing a bone fraction image. The bone fraction image can be computed by material separation of a scan from a dual layer detector or other spectral imaging equipment, or from a forward projection of an intermediate first pass reconstruction of a single energy scan image.

In this embodiment the image processing system includes a tissue determiner TID to compute the tissue image, such as the bone image. In this embodiment with tissue type refinement, the kernel selection is refined by using a weighted scheme with a factor derived from the tissue image such as the bone fraction image. In more detail, higher bone fractions lead to smaller weighting factors for the scatter kernels. In embodiments, the bone fraction information per image location is mapped to the weighting factor ("bone fraction image") that describes the relative amount of bone in the path between focal spot and image location.

Figure 6:
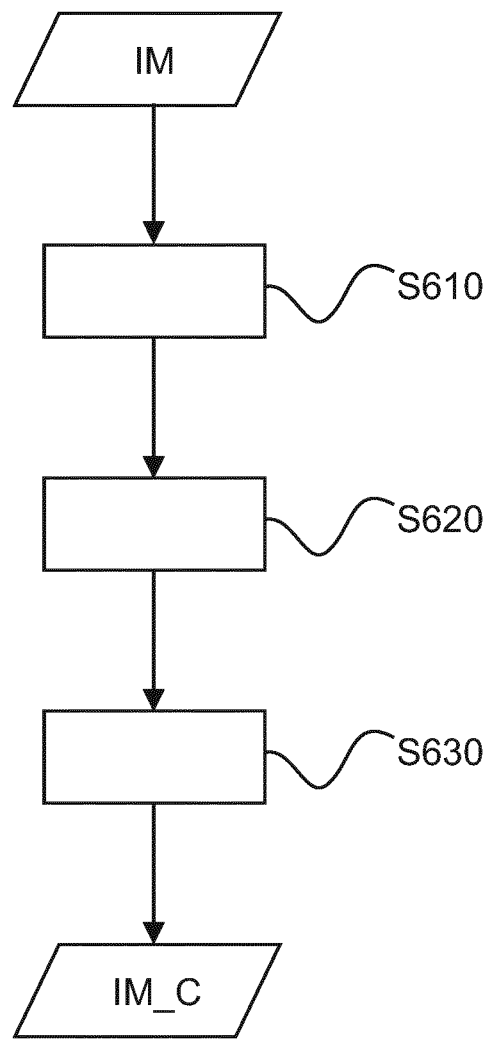
FIG. 6 shows a flow chart of a method for image processing according to one embodiment.

Reference is now made to flow chart in FIG. 6 to describe a method of image processing as implemented by the image processing system IPS. However, it will be understood that the steps described in the following are not necessarily tied to the architecture of the image processing system IPS as described above but the following steps may also be understood as a teaching in its own right.

At step S610, an input X-ray image IM to be scatter-corrected is received. The input image IM can be retrieved from an image database, such as a PACS (picture archiving and communication system) in a HIS (hospital information system) or can be supplied direct from the X-ray imaging apparatus.

The input image IM to be scatter-processed may be received wirelessly or through a wired connection. The input X-ray image IM is either a projection image from projection domain or may be a reconstructed image in imaging domain, reconstructed by a reconstruction algorithm from projection imagery. If the input image is a reconstructed one, the scatter correction is preferably still applied to the projection imagery. The input image IM may be 2D or 3D. The image IM may be acquired of an object, such as a region of interest of a human or animal subject, such as a skull, chest or heart, or other. In some instances, a suitable contrast agent is injected beforehand to increase contrast for soft tissue.

The proposed method is based on a refined signal model to account for single and multiple scatter events, respectively.

To this end, in step S620, respective kernels for scatter correction are provided to account for multiple scatter and single scatter, respectively. In other words, at least two different kernel types are provided. The providing of the kernels, may include selecting from a library of pre-computed kernels or may include computing the kernels on demand on the-fly. Selection from the library of pre-determined kernels may include interpolation from existing pre-computed kernels. Providing the kernels separately in different procedures allows optimizing for each of multiple and single scatter.

Step S620 for providing the two different types of kernels, one for multiple scatter and one for single scatter, uses preferably a local approach for selecting the single scatter kernel and a global approach for selecting the multiple event scatter kernel. A local approach for the selecting multiple scatter kernels is also envisaged.

Specifically, in embodiments, step S620 for providing kernels of the first or second type includes finding best-matching (based on a measure d) existing or interpolated kernels to local image properties around an image location in a patch. The said properties include the intensity values recorded in the patch and/or gradients. In embodiments the selection for the multiple scatter event kernel includes matching against the whole image rather than the individual image patches.

If matching against local image properties in image patches is employed, this may be done for each and every single image location but may also be done in a more coarse-grained approach where only a sub-selection, but not all image locations, are considered. For instance, a random or other selection (every other or every k-th pixel in one or both spatial directions x,z) may be made. In the random mode, a suitable random generator is run to select randomly a certain number of image locations for analysis to match the kernels for at least one of the single or multiple scatter situation. In a further variation of this, the whole image is divided into sub-portions and the matching is carried out only in those sub-portions. For instance, the image may be divided into k quadrants, such as 4, eight or more quadrants. Matching is then done quadrant-wise. Other sub-divisions are also considered to speed up the kernel selection procedure. In addition or instead, the input image may be down-sampled first and step S620 is then performed on the down-sampled input image.

The database as envisaged herein holds a set of kernels for the single scatter event category and a different set of kernels for the multiple scatter event category. In each category, the kernels may be further distinguishable by size, shape or other of the associated phantom WS. Specifically, and in one embodiment, the kernels are based on water ball models as reported by Applicant in WO2007/148263 A1. However, other prototype phantoms based on models other than water and/or shapes other than balls are also envisaged in alternative embodiments. In particular, cylindrical or ellipsoidal shaped phantoms (based on water properties or other material) are specifically envisaged for the multiple scatter event type kernels as will be detailed further below.

Turning now first in more detail to kernel selection for the single scatter event type, this can be done as in the above mentioned local approach by defining for a given image location an image patch. Matching is then done based on the intensity values and/or gradient values in the image. The image patch is matched to the respective ideal image associated with each of the kernels in the first category. Any optimization scheme can be used to find the best match. A cost function can be set up that measures based on a suitable measure d, how the local patch and the point spread image PSF differs. Kernel parameters i for a best match, or at least a match better than a threshold is then determined in the optimization, and the associated kernel is then selected and provided as the kernel for single scatter event estimation. The kernel parameterization based on which the optimization is run includes for instance (T, $\phi$, R) as mentioned above, or other depending on the shape of the kernels.

In step S620, when matching against kernels from the second category (that is, multiple scatter event type kernels), the following embodiments are envisaged.

One embodiment is still local as above for the first category selection, but in this embodiment the image is first subjected to a low pass filtering. With this low pass filtering any structures more typical for local scatter are removed or at least suppressed to form the flattened image introduced above. For the purpose of multiple scatter event type kernel selection, this low pass filtering may be done in addition to any filtering done further up-stream in the single processing chain from acquisition. In particular, this filtering may be done in addition to other filtering done before the first category kernel selection. In embodiments, the filtering is local, that is, the filtering is applied for each patch individually, with individually adjusted filter coefficients and filter kernels before performing the matching against the respective patch. Alternatively, the whole image is filtered globally with the same filter coefficients. The filtering may be user adjustable. The exact filter parameters can be obtained experimentally by examining scatter artefacts and by adjusting the filter parameters to reduce the artefacts. Automated test protocols may be used to do this efficiently.

In addition or instead of the filtering, the flattened image may be formed by forming a gradient image and to threshold the gradient values against a fixed, or user adjustable, threshold to eliminate high gradients to so clip high gradients. The result of either the filtering or clipping is a structurally flattened image which is then matched patch-wise to the kernels in the selection procedure, as explained. The selection is either an optimization over the parameters in parameter space as in eq (1), (2) or is based on a simpler comparison loop through the kernels in the database using suitable measure d(.,.) for comparison to find the best matching kernel.

In alternative embodiments, a more global approach is used, according to which the whole image is matched against the second category type kernels. In this embodiment the phantom shape is preferably chosen to match the region of interest to be imaged. For instance, for head imaging a ball shaped phantom is chosen about the size of a human head. For chest imaging an ellipsoidal shape phantom is used with axes commensurate to the patient chest measurements, and similar for other geometries of other ROIs. In other words, in this global approach, only a single set of phantom parameters i is determined (for the whole image) to estimate for multiple scatter. This single best phantom may be found by matching relative to only a subset of all parameters i, such as only based on size components. This single best phantom may then be locally adjusted to respective image locations j. In embodiments, this local adjustment may be done as in eq (1), (2) but for the second category kernels and with optimizing only for the other the parameters i (that is, the set-complement of the size components).

In combination with any of the above kernel provision/selection schemes, step S620 may also include determining a tissue type in the region of interest and then to further optimize the selection, not only based on first or second category type kernels, but also on tissue type. To this end, the distribution of the issue type as per the input image IM is estimated. One particular tissue type of interest and relevant for scatter are relatively high density tissues such as bone. To estimate bone distribution, a bone fraction image may be determined in step S620 as explained above in relation to FIGS. 1-5. Depending on the bone fraction a factor may be applied to the respective first and/or second category kernels found in the optimization as mentioned above. The factor is applied to the water based kernel to account for the different scatter properties of bone and water. The weighting factor can be calculated offline, e.g. by using MC simulations, or may be derived from the scatter cross sections of bone and water. In an alternative embodiment, the bone density fraction is an additional parameter of the pre-computed kernel set, i.e. the kernel set includes kernels for all possible bone fraction (e.g., 10%, 20%, etc). The bone density fraction is then used as an additional parameter (in addition to the spatial parameterization) when performing the kernel selection.

Once at least two kernels for single and multiple scatter events have been found, each possibly with multiplied with a factor according to tissue distribution, these then constitute an estimate for the respective single and multiple scatter event contributions. The kernels may then be subtracted from the initial image in correction or the correction with the kernels may be done otherwise. This step is based on the model proposition that the scatter corruption as encoded in each image value of the original image is made up from additive contributions from each multiple scatter and single scatter. Accordingly, in error correction step S630, the PSFs for single and multiple scatter are applied to the input image IM, such as being subtracted from the input image IM, to obtain the corrected image IM_C. The so scatter corrected image IM_C can then be displayed on a display device, stored for further reference or otherwise processed.

As a variation to the above described step S620, once the first category kernels have been found, these can be subtracted from the initial input image to form a partially corrected image IM_$C_p$. This image is partially corrected because at this stage the image IM has been corrected only for single scatter events. The matching for finding the second category kernels is then done against this partially corrected image IM_$C_p$ and once the second category kernel (s) has been found, this is then subtracted from the partially corrected image IM_$C_p$ to produce the (now fully) corrected image IM_C. This approach may be reversed, that is, it is the second category kernels that are determined first and then subtracted from the initial image IM to form the partially corrected image IM_$C_p$. It is then this partially corrected image IM_$C_p$ that is then used to find the first category kernels as above described.

It will be understood that the above described step S620 and S630 may be performed iteratively in a fixed number or steps or until sufficient convergence is established. In other words, once in step k, the scatter corrected image IM_$C^k$ is obtained, this is then fed back to step S620 as a new input image to then obtain in the same fashion a new scatter corrected image IM_$C^{k+1}$=IM_$C^k$-$\Sigma_j K^{1,j}$+$\Sigma_j K^{2,j}$), where the kernels $K^{1,j}$, $K^{2,j}$ are obtained in matching against IM_$C^k$ from the earlier cycle.

In all of the above embodiments, when applying the correction in step S630, instead of using a subtractive scheme as per eqs (3), (4) above, a multiplicative scheme is also envisaged in alternative embodiments where IM_C= (IM$^2$)/(IM+$\Sigma_j K^{1,j}$+$\Sigma_j K^{2,j}$), similar to what was reported earlier in Applicant's US 2010/0189376, eq (11). When done iteratively, the multiplicative scheme may be written as IM_$C^{k+1}$=(IM*IM_$C^k$)/(IM_$C^k$+$\Sigma_j K^{1,j}$+$\Sigma_j K^{2,j}$), where, again, kernels $K^{1,j}$, $K^{2,j}$ are obtained in matching against IM_$C^k$ from the earlier cycle. The multiplicative approach allows avoiding negative values, thus making the procedure more robust.

Although in the above a distinction has been made between single and multiple scatter events, a more general distinction may be considered where scatter made up from up to N (a natural number>1) events forms one category whilst the second category is formed by scatter made up from more than N scatter events. Indeed, in one embodiment this can be further generalized by not considering only two categories but M different categories each category comprising scatter events within a certain range. This may allow further refining the signal model to better account for certain scatter types involving scatter events in a certain range.

The components of the image processing system IPS may be implemented as software modules or routines in a single software suit and run on a general purpose computing unit PU such as a workstation associated with the imager IM or a server computer associated with a group of imagers. Alternatively, the components of the image processing system IPS may be arranged in a distributed architecture and connected in a suitable communication network. The IPS may be fully integrated into the X-ray imaging apparatus.

It should be appreciated that the terms "optimization" or "optimizer" as used above to find the best matching phantom (and hence kernel) are based on a numerical optimization scheme/algorithm, examples for which were mentioned above. However, use of any of these does not necessarily imply that the output is optimal in an absolute sense. For one reason, the algorithm used may not necessarily converge during iteration towards a global minimum but may converge to a local minimum. Second, the iterations herein may be aborted after a few iterations, to save resources or for whatever reason. For instance, one abort condition may be that iterations are to halt if there is no significant change at the output after a pre-defined number of iteration steps. Furthermore, although the above optimizations have been formulated in terms of minimization of cost function F, this is not limiting as equivalent formulations in terms of maximization of a utility function may be preferred in other contexts or setups and these are equally envisaged herein in embodiments.

Some or all components of the IPS may be arranged in hardware such as a suitably programmed FPGA (field-programmable-gate-array) or as hardwired IC chip.

One or more features of the IPS disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray image processing system, comprising:
    an input interface for receiving an image of an object acquired by an imaging apparatus;
    a kernel provider configured to provide respective scatter kernels for at least two scatter types; and
    a scatter correction module configured to perform a correction in the image based on the provided at least two kernels, wherein the at least two scatter types include a different number of scatter events, wherein one of the scatter types includes a single scatter event and the other scatter type includes multiple scatter events, wherein the kernel provider is configured to select or compute the at least two kernels differently, wherein the kernel provider is configured to provide at least one kernel for multiple scatter events based on a clipped signal gradient in a patch of the image by clipping image gradient values at a pre-defined threshold.

2. The system of claim 1, wherein the kernel provider is configured to select or compute at least one kernel for a single scatter event based on at least one of signal strength and signal gradient in the patch.

3. The system of claim 1, wherein the kernel provider is configured to provide the at least one kernel for multiple scatter events based on low-pass filtering the image and the signal strength or gradient in the patch.

4. The system of claim 1, wherein the kernel provider is configured to provide the at least one kernel for multiple scatter events based on signal strength and/or signal gradient of the image.

5. The system of claim 1, wherein the kernel provider is configured to provide at least one of the kernels based on a physical characteristic of the object.

6. The system of claim 5, wherein the kernel provider is configured to provide the at least one kernel for multiple scatter events based on a shape of at least a part of the object.

7. The system of claim 1, wherein the kernel provider is configured to provide at least one of the kernels based on a library of pre-computed kernel.

8. The system of claim 1, comprising a tissue determiner configured to determine a tissue type based on the image, wherein the kernel provider takes the tissue type into account when providing at least one of the at least two kernels.

9. A method for X-ray image processing, comprising:
    receiving an image of an object acquired by an imaging apparatus;
    providing, by a kernel provider, respective scatter kernels for at least two scatter types, wherein the at least two scatter types include a different number of scatter events, wherein one of the scatter types includes a single scatter event and the other scatter type includes multiple scatter events;
    selecting or computing the at least two kernels differently;
    providing at least one kernel for multiple scatter events based on a clipped signal gradient in a patch of the image by clipping image gradient values at a pre-defined threshold; and
    performing a correction in the image based on the provided at least two kernels.

10. A non-transitory computer-readable medium having executable instructions stored thereon which, when executed by at least one processor, cause the at least one processor to perform a method for X-ray image processing, the method comprising:
    receiving an image of an object acquired by an imaging apparatus;
    providing, by a kernel provider, respective scatter kernels for at least two scatter types, wherein the at least two scatter types include a different number of scatter events, wherein one of the scatter types includes a single scatter event and the other scatter type includes multiple scatter events;

selecting or computing the at least two kernels differently;
providing at least one kernel for multiple scatter events based on a clipped signal gradient in a patch of the image by clipping image gradient values at a predefined threshold; and
performing a correction in the image based on the provided at least two kernels.

* * * * *